United States Patent
Fernandez Gines

(10) Patent No.: US 9,554,998 B1
(45) Date of Patent: Jan. 31, 2017

(54) COMPOSITION OF ANALGESIC BIOADHESIVE HEALING MICROSPHERES

(71) Applicant: Damaso Fernandez Gines, Alicante (ES)

(72) Inventor: Damaso Fernandez Gines, Alicante (ES)

(*) Notice: Subject to any disclaimer, the term of this patent is extended or adjusted under 35 U.S.C. 154(b) by 0 days.

(21) Appl. No.: 14/817,231

(22) Filed: Aug. 4, 2015

(51) Int. Cl.
*A61K 9/16* (2006.01)
*A61K 31/08* (2006.01)
*A61K 9/51* (2006.01)

(52) U.S. Cl.
CPC ........... *A61K 9/1676* (2013.01); *A61K 9/1641* (2013.01); *A61K 9/1652* (2013.01); *A61K 9/5153* (2013.01); *A61K 31/08* (2013.01)

(58) Field of Classification Search
CPC .... A61K 9/5153; A61K 9/1641; A61K 31/08; A61K 9/1652
See application file for complete search history.

(56) References Cited

U.S. PATENT DOCUMENTS

| | | | |
|---|---|---|---|
| 6,415,019 B1* | 7/2002 | Savaglio | H04M 3/42314 379/37 |
| 2011/0027331 A1 | 2/2011 | Hobot | |

FOREIGN PATENT DOCUMENTS

| | | |
|---|---|---|
| WO | 2009094459 A1 | 7/2009 |
| WO | 2014143964 A2 | 9/2014 |

OTHER PUBLICATIONS

N. Boucard, et al; The use of physical hydrogels of chitosan for skin regeneration following third-degree burns; ScienceDirect; Biomaterials; vol. 28; 2007; pp. 3478-3488.
A. Fassoulaki, et al; Skin application of isoflurane attenuates the responses to a mechanical and an electrical stimulation; Reports of Investigation; Canadian Journal of Anaesthesia; vol. 45; No. 12; 1998; pps. 1151-1155.
European Search Report dated Sep. 23, 2016 for corresponding Application No. 16182326.5-1460.

* cited by examiner

*Primary Examiner* — Kyle Purdy
(74) *Attorney, Agent, or Firm* — Lucas & Mercanti, LLP

(57) ABSTRACT

A new composition of analgesic bioadhesive healing microspheres in which each microsphere comprises at least:
a.—a layer of a polyanion, where the polyanion may be an alginate.
b.—a core coated with a polyanion consisting of a triblock copolymer non-ionic surfactant; poloxamer 188 or a mixture of them; and a volatile halogenated by-product anesthetic ether agent of methyl-isopropyl-ether in contact with the internal part of the polyanion layer, which may be sevoflurane.
c.—a coating of a polycation in contact with the external part of the polyanion layer, which may be chitosan.

1 Claim, No Drawings

COMPOSITION OF ANALGESIC BIOADHESIVE HEALING MICROSPHERES

THE SUBJECT OF THE INVENTION

This invention refers to a new pharmaceutical composition, cost-effective in production, for algic treatment and to enhance healing of cutaneous lesions or of the oral mucosa where the healing process deteriorates and with loss of substance, epithelium and/or conjunctiva, comprising microspheres composed of a triblock copolymer non-ionic surfactant core or a mixture, such as poloxamer 188, and a volatile halogenated ether agent such as fluoromethyl 2.2.2-trifluoro-1-(trifluoromethyl)ethyl ether; a layer of polyanion such as sodium alginate; and a coating of polycation such as chitosan.

PRIOR ART 2.5 million cases of chronic ulcer (of venous and arterial etiology) in the lower limbs are registered annually in the United States. Their presence is associated with pain, restriction on work activities and leisure, reduced mobility, sleep disorders, reduced psychological well-being and social isolation. They also represent a major financial burden for healthcare systems.

The lack of trials in medical interventions intended to relieve the persistent pain associated with vascular ulcers is discouraging in the light of the evidence of the degree and impact of pain in those with this condition (Briggs et al Topical agents or dressings for pain in venous leg ulcers. Cochrane Database Syst Rev. 2012; 14; 11:CD001177).

The topical anesthetic most studied is the eutectic lidocaine-prylocaine cream. This demonstrates an improvement compared with a placebo in relieving basal pain or following debridement in this pathology, with the use of eutectic lidocaine-prylocaine cream or with slow-release ibuprofen in foam dressings, and evidence of association with adverse effects such as itching and a burning sensation with use of the cream. (Briggs et al Topical agents or dressings for pain in venous leg ulcers. Cochrane Database Syst Rev. 2012; 14; 11:CD001177). The work of Tran and Koo et al. confirms an increase of systemic toxicity from treatments with topical anesthetics over long periods of time, dealing with vascular conditions, so that the use of lidocaine-prylocaine for this pathology may be contraindicated. There is at present a lack of scientific evidence about the effectiveness of the various topical treatments for the pain associated with vascular ulcers.

Currently the pharmaceuticals most used in normal medical practice to manage pain in chronic ulcers are COX I, II and III inhibitor analgesics, various coanalgesics and coadjuvants.

These pharmaceuticals are classified as first stage (AINES), second (mild opioids, associated or not associated with AINES) and third stage, such as powerful opioids.

They are prescribed for these patients according to the basic principles of the analgesic ladder, making initial use of non-opiate analgesics very frequent because of their central and peripheral effects, most of them moderated by the inhibition of prostaglandin synthesis.

Use of these analgesics in our healthcare system is widespread as they are not associated with respiratory depression, tolerance or physical dependence.

Their analgesic effectiveness is limited, in other words they have an analgesic ceiling, their analgesia not being dose-dependent, so that increased dose may prolong the effect but does not produce more analgesia and raises the incidence of side effects.

They are effective in the treatment of slight-moderate pain and in some cases may control intense pain with an inflammatory component, but the use of anti-inflammatory non steroid drugs and opiates in the elderly population with a high associated comorbility is accompanied by a high rate of adverse effects.

A decision to use a product to relieve a symptom such as vascular ulceration pain must be considered along with the primary objective, which is the healing of the ulcer.

Any intervention which relieves pain but significantly slows healing is likely to prove clinically unacceptable, unless it is clear that the ulcer is very unlikely to heal.

In such circumstances, symptom control would become the primary objective. If the ulcer is very painful, doctor and patient might agree that a delay in the healing is an acceptable "price" to be paid in exchange for a reduction of the pain.

It can thus be asserted that there is not at present an effective treatment for chronic vascular ulcers with tendency to torpid evolution.

Research is needed on new compounds to treat this pathology.

The halogenated anesthetics isoflurane and sevoflurane are halogenated ether by-products, normally administered by inhalation to attain or maintain the patient's hypnotic state, although their precise mechanism of action as hypnotic has not yet been clarified.

In addition to their hypnotic effect on the nervous system, their analgesic effect has also been demonstrated at the central level, but research intended to find a peripheral-level analgesic effect has failed, so that they are at present considered to lack such effect.

Fassoulaki et al. applied isoflurane, halothane and sevoflurane for 30 minutes to the forearms of healthy volunteers and found a slight local analgesic effect. Chu et al. observed an analgesic effect whose intensity was dose-dependent.

From a histological standpoint, injecting a substance subcutaneously is similar to irrigating it on the wound bed where there is no skin, so that a barrier effect cannot be produced and the free nerve-ends left exposed.

2011 saw the publication of the first case (M. Gerónimo-Pardo et al) of a patient with a very painful vascular ulcer, where the therapy was based on different combinations of analgesics (such as paracetamol, metamizole, tramadole, morphine, fentanyl, buprenorphine, pregabalin and gabapentin, as well as applications of eutectic lidocaine/prylocaine and infusion of epidural ropivacaine), and was completely unsatisfactory.

Analgesic control was finally achieved with the application of liquid sevoflurane directly on to the ulcer bed, providing immediate, intense and long-lasting analgesia.

To patients' satisfaction, the same response was obtained throughout the 16 days the ulcer took to heal. Just two projects follow supporting this first one (Martinez et al and Gerónimo, the three in the article on emergencies).

Fluorocarbonated molecules with a high number of fluoride atoms have been shown to have the capacity to transport oxygen and so have been used as blood substitutes, popularly known as synthetic blood.

Because of the similarity of the volatile halogenated ether agent's molecule and fluorocarbons with a high number of fluoride atoms, it has been proposed that the volatile halogenated ether agent may increase the amount of oxygen exposed to the cells in the area of the damaged tissue, enhancing the healing process and helping to avoid the intense catabolism produced in the damaged tissue.

In addition, the antimicrobial effect of the volatile halogenated ether agent on tissue over-infected by multi-resistant *Pseudomona aeruginosa* has also been suggested, a bactericide effect also having been observed in vitro against *Staphylococcus aureus, Pseudomona aeruginosa* and *Escherichia coli* (Martinez Monsalve et al). This antimicrobial effect of the volatile halogenated ether agent also brings with it the reproduction of conditions favourable to the healing process in the damaged tissue.

Thus, given the importance of pain control and the healing of chronic vascular ulcers, and the lack of effective treatments described in the current medical literature, the need arises to create a system of modified release for the treatment of cutaneous lesions, for reasons of security and effectiveness.

DESCRIPTION OF THE INVENTION

The invention refers in one aspect to a microsphere comprising the following:

(i) a polyanion layer;

(ii) a core coated with a polyanion consisting of a triblock copolymer non-ionic surfactant and a halogenated by-product volatile anesthetic agent of methyl-isopropyl-ether in contact with the internal part of the polyanion layer;

(iii) a coating of a polycation in contact with the external part of the polyanion layer.

This microsphere offers analgesic and healing properties making it useful in the treatment and/or prophylaxis of an algic process with deterioration of the cutaneous healing process or of the oral mucosa in an animal, including man as necessary.

Thanks to this application as medication, the materials making up the microspheres used as releasing agents of the volatile ether agent are preferably biocompatible, biodegradable and bioadhesive.

Thus the polyanion might in principle be any conventional polyanion which is biocompatible and biodegradable.

In a preferred embodiment of the invention, the polyanion is selected from the group formed by alginate, polyglycolic acid, polyglycolic acid copolymer and lactic acid, agarose, polyacrylates, carrageenans and their mixes.

In one particular embodiment, the polyanion is alginate.

The alginate which may be used in this invention may be from any source, bacterial and/or brown seaweeds, and can be obtained for example commercially in the form of a mixture of sodium, potassium, calcium and magnesium salts.

These are heterogeneous macromolecular forms whose structures are not repeated regularly, and comprising L-glucoronic acid (G) and D-mannuronic acid (M) monomers, generating blocks within the structure called G-blocks, M-blocks and GM-blocks of varying flexibility. In this sense it has been observed that the unions forming the structures of the L-glucoronic acid dimers allow the polycation to adhere better.

In the alginate the fractions of G and M (fm and fg) vary depending on their source and subsequent treatment. In one preferred embodiment, the alginate used has at least 70% fraction G.

The triblock copolymer non-ionic surfactant is selected from the group formed by poloxamer 108, poloxamer 123, poloxamer 124, poloxamer 188, poloxamer 217, poloxamer 237, poloxamer 238, poloxamer 288, poloxamer P 338 and poloxamer 407 and/or a mixture of them. Poloxamers are non-ionic triblock copolymers comprising a central hydrophobic polyoxypropylene chain flanked by two hydrophilic polyoxyethylene chains.

Because of their amphyphylic structure, polymers have tensioactive properties which make them useful in industrial applications.

They can be used among other things to increase the water solubility of hydrophobic or oily substances or otherwise increase the miscibility of two substances with different hydrophobicities.

Thus these polymers are commonly used in industry, cosmetics and pharmaceutical products.

Poloxamers are generally known for not demonstrating toxicity, and being non-irritant.

In one particular embodiment, the triblock copolymer non-ionic surfactant used is poloxamer 188.

The volatile halogenated agent can in principle be any halogenated hydrocarbon, more specifically the halogenated ethers.

The particular embodiment of the invention selects the group of halogenated ethers formed by isoflurane, methoxyflurane, enflurane, sevoflurane and desflurane or a mixture of these.

In a particular embodiment, the volatile halogenated ether used is sevoflurane.

The polycation may in principle be any conventional biocompatible and biodegradable polycation.

In a particular embodiment of the invention, the polycation is selected from the group formed by poly-L-lysine, heparin, polyethylene glycol, chitosan, poly-L-omitin, conventional synthetic polymers such as poly-methylene-co-guanidine and poly-ethylene-amine for example, and mixes of these.

In one particular embodiment, chitosan is the polycation used.

In principle, the microspheres can be obtained by various conventional procedures from the prior art, varying depending on the structure.

In one particular embodiment, microspheres are obtained which comprise a triblock copolymer non-ionic surfactant core along with the volatile halogenated ether agent, a layer of polyanion and a polycation coating, according to the procedure described below and which comprises the following stages:

a.—preparation of an emulsion of a polyanion, a triblock copolymer non-ionic surfactant and the volatile halogenated ether agent in distilled water; a solution of a polycation in distilled water and a dissolution comprising at least one divalent cation;

In stage a) the polyanion dissolution is prepared to a concentration typically between 0.5 and 4% in weight of polyanion in distilled water; the triblock copolymer non-ionic surfactant is prepared to a concentration typically between 0.1 and 55% in weight of non-ionic copolymer triblock surfactant in distilled water; the volatile halogenated ether agent solution is prepared to a concentration typically between 0.01 and 65% in volume of volatile halogenated ether agent in distilled water; the polycation solution is prepared to a concentration typically between 0.1 and 2% in weight in distilled water and the dissolution comprising at least one divalent cation may for example comprise Ca, Sr, Ba or mixtures of them, typically to a concentration of between 20 and 100 nM in distilled water. During stage a) magnetic agitation is held constant at a speed of 100-1500 r/min.

b) Obtaining polyanion microspheres by placing the polyanion emulsion and divalent cation in contact; the microspheres are obtained from the polyanion emulsion with generation of a microdroplet of the polyanion emulsion, submitted to electrostatic potential. The microdroplet fragments and drops into the dissolution containing the divalent cation. The microspheres obtained are formed by polyanion stabilised by ionic bonds. These microspheres then come into contact with the polycation solution to obtain the polyanion-polycation microspheres by electrostatic attraction, creating a three-dimensional structure of chains rich in guluronic acids of the polyanion in coordination with the calcium of the polycation, generating a final structure called an "egg-box".

c) the polyanion microspheres obtained in stage b) are put in contact with the polycation solution; and d) the microspheres are obtained (polyanion-polycation microspheres).

In a particular embodiment of this procedure, the polyanion emulsion microdroplets are formed by sending the emulsion through a connection by extraction from a syringe containing it, driven by a permanent syringe infusion pump.

The emulsion flows through an extrusion needle (the cone unbevelled) at a perfusion typically of 7 ml/hour. The microdroplet generated at the needle point is submitted to a potential generally of 5,000-10,000 V in a device where the needle is the positive pole and a copper ring the negative pole, and with a distance of 6 cm between the needle point and ring.

The microdroplet submitted to the potential fragments and falls into the dissolution containing the cation and which, like the polyanion emulsion, is agitated continuously.

The divalent ions disperse in the polyanion emulsion to form microspheres comprising polymer stabilised by ionic bonds.

The microspheres are retained for some time in the dissolution, are washed with abundant distilled water and are then placed in the polycation suspension.

They are held typically for 2 hours, the polycation layer formed by electrostatic attraction.

The polyanion-polycation microspheres formed behave like a semipermeable membrane, where the polyanion-polycation complex gives it mechanical stability, the electropositivity determined by the polycation.

The size of the microsphere in the invention varies, within wide margins, generally between 50 and 5000 microns, preferably between 100 and 900 microns and more preferably between 200 and 600, depending on the following control parameters: a) the concentration of polyanion in the dissolution; in general, the lower the concentration the smaller the size; b) the diameter of the extrusion needle (smaller diameter, smaller size). For sizes less than 500 microns, bores of less than 1 mm (of the needle) are required; and c) the voltage and difference of potential between the needle and the copper ring (the greater the potential difference, the smaller the size).

In the practical application of this invention, any of the agents used to produce the sphere for treatment of cutaneous lesions must be inert, that is compatible with the volatile halogenated ether agent.

The agents used particularly by the inventor give the sphere core, where the volatile halogenated ether agent is located, long-lasting physical-chemical stability of at least 90 days at temperatures of 2-8° C.

The physical-chemical stability is studied using Nuclear Magnetic Resonance (NMR), the NMR spectra acquired with a Bruker Avance DRX 300 MHz® spectrometer with a 5 mm single-axis z-gradient quattro core probe (Bruker Biospin GmbH, Rheinstetten, Germany).

The International Cosmetic Ingredient Dictionary & Handbook, Fifteenth Edition (2014) describes a wide range of ingredients commonly used in the skincare industry.

Examples of such types of ingredients include: fragrances, colorants (for example bright blue, bright cresyl blue, allura red and titanium dioxide), antioxidants (for example BHT and tocopherol), chelating agents (for example disodium EDTA and tetrasodium EDTA), preservatives (for example, methylparaben, propylparaben and phenoxyethanol), pH adjustors (for example sodium hydroxide, triethanolamine, phosphoric acid and citric acid), buffers (for example citrate and phosphate), absorbents (for example aluminium starch octenylsuccinate, kaolin, corn starch, oat starch, cyclodextrin, talc and zeolite), skin whiteners and agent lighteners (for example hydroquinone and niacinamide lactate), moisteners (for example glycerine, propylene glycol, butylene glycol, pentylene glycol, sorbitol, urea, and mannitol), emollients (for example mineral oil, vaseline, isopropyl myristate, cyclomethicone and vegetable oil), exfoliants (for example alpha-hydroxyacids and beta-hydroxyacids such as lactic acid, glycolic acid, salicylic acid and their salts), waterproofing agents (for example magnesium/aluminium hydroxide stearate), skin conditioners/hydrating agents (for example extracts of aloe, allantoin, bisabolol, ceramidase, dimethicone, hyaluronic acid and dipotassium glycyrrhizate), tensioactive agents (for example ethoxylated alcohol, ethoxylated fatty esters and oils, quaternary tensioactive substances and alcohol sulphates), and rheology modifiers (for example sodium polyacrylates, carbomers, natural rubbers, natural rubber by-products, clays, modified clays, cellulose, microcrystalline cellulose, cellulose by-products, magnesium aluminium silicates, gellan gum, xanthan gum, starches and modified starches).

Additional ingredients can be incorporated in an aqueous mixture of the polyanion using various procedures, including methods known in the technique, depending on the characteristics of such additional ingredient.

For example, the agent can be incorporated with the aqueous solution and polyanion before it is combined with the triblock copolymer non-ionic surfactant.

Alternatively, the agent can be incorporated after adding the triblock copolymer non-ionic surfactant together with the polyanion in the aqueous phase.

The invention claimed is:

1. A composition of analgesic bioadhesive healing microspheres comprising:
   a.—a layer of a polyanion;
   b.—a core coated with said polyanion, said core consisting of a triblock copolymer non-ionic surfactant and a halogenated volatile by-product anesthetic agent of methyl-isopropyl-ether, wherein said core contacts the internal part of the polyanion layer;
   c—a polycation coating in contact with the external part of the polyanion layer;
   where the polyanion is selected from the group consisting of alginate, polyglycolic acid, a copolymer of polyglycolic acid and lactic acid, agarose, polyacrylates, carrageenans and their mixtures thereof;
   where the triblock copolymer non-ionic surfactant is a poloxamer;
   where the halogenated ether is selected from the group consisting of isoflurane, methoxyflurane, enflurane, sevoflurane, desflurane, or mixtures thereof;

where the polycation is selected from the group consisting of poly-L-lysine, heparin, polyethylene glycol, chitosan, poly-L-omitin, conventional synthetic polymers selected from poly-methylene-co-guanidine and poly-ethylene-amine, and mixtures thereof.

* * * * *